US006839584B2

(12) United States Patent
Makarewicz et al.

(10) Patent No.: US 6,839,584 B2
(45) Date of Patent: Jan. 4, 2005

(54) METHOD AND APPARATUS FOR MINIMIZING SPECTRAL INTERFERENCE DUE TO WITHIN AND BETWEEN SAMPLE VARIATIONS DURING IN-SITU SPECTRAL SAMPLING OF TISSUE

(75) Inventors: Marcy Makarewicz, Chandler, AZ (US); Mutua Mattu, Gilbert, AZ (US); Thomas B. Blank, Chandler, AZ (US); George Acosta, Phoenix, AZ (US); Edward Handy, Chandler, AZ (US); William Hay, Gilbert, AZ (US); Timothy Stippick, Tempe, AZ (US); Benjamin Richie, Scottsdale, AZ (US)

(73) Assignee: Instrumentation Metrics, Inc., Chandler, AZ (US)

( * ) Notice: Subject to any disclaimer, the term of this patent is extended or adjusted under 35 U.S.C. 154(b) by 9 days.

(21) Appl. No.: 09/954,856

(22) Filed: Sep. 17, 2001

(65) Prior Publication Data

US 2002/0099278 A1 Jul. 25, 2002

Related U.S. Application Data

(63) Continuation-in-part of application No. 09/563,782, filed on May 2, 2000, and a continuation-in-part of application No. 09/631,440, filed on Aug. 2, 2000.
(60) Provisional application No. 60/235,424, filed on Sep. 26, 2000.

(51) Int. Cl.[7] .............................................. A61B 5/00
(52) U.S. Cl. ..................... 600/344; 600/310; 600/340
(58) Field of Search ................. 600/322–326, 600/334–335, 344, 340, 336

(56) References Cited

U.S. PATENT DOCUMENTS 3,785,196 A  *  1/1974  Smith ........................ 73/53.05
5,111,817 A     5/1992  Clark et al. ................. 128/633
5,195,985 A  *  3/1993  Hall ............................ 604/195
5,368,025 A  * 11/1994  Young et al. ................ 600/310
5,671,317 A  *  9/1997  Weishaupt et al. .......... 385/137
5,830,132 A    11/1998  Robinson .................... 600/310
5,991,648 A    11/1999  Levin .......................... 600/344
6,026,313 A     2/2000  Kexin ......................... 600/310
6,039,697 A  *  3/2000  Wilke et al. ................. 600/532
6,064,897 A  *  5/2000  Lindberg et al. ............ 600/316
6,078,828 A  *  6/2000  Yasuda et al. ............... 600/310
6,088,605 A  *  7/2000  Griffith et al. .............. 600/316

OTHER PUBLICATIONS

Webster's II New Riverside University Dictionary, The Riverside Publishing Co., 1994, p. 755.*

* cited by examiner

*Primary Examiner*—Eric F. Winakur
*Assistant Examiner*—Matthew Kremer
(74) *Attorney, Agent, or Firm*—Glenn Patent Group; Michael A. Glenn

(57) ABSTRACT

An apparatus and method for reproducibly interfacing a living tissue sample to the measurement probe of a spectrometer instrument in-situ minimizes spectral interference related to sampling variations. A minimal contact subject interface includes supports replaceably mounted on a base. An optical coupling means, such as a fiber optic probe, contacts the measurement site through a probe aperture in the base. During use, a subject rests an extremity on the support elements, so that the extremity is reproducibly positioned and supported in relation to the optical coupling means. The supports have a small contact area, minimizing contact with the skin at the measurement site. The interface module is adjustable to fit any subject.

By reproducibly positioning and supporting the body appendage using minimal contact supports, spectral interference due to variations in placement, applied pressure, and temperature transients secondary to contact with the interface module are greatly minimized.

55 Claims, 1 Drawing Sheet

METHOD AND APPARATUS FOR MINIMIZING SPECTRAL INTERFERENCE DUE TO WITHIN AND BETWEEN SAMPLE VARIATIONS DURING IN-SITU SPECTRAL SAMPLING OF TISSUE

CROSS REFERENCE TO RELATED APPLICATIONS

This application claims benefit of U.S. Provisional Patent Application Ser. No. 60/235,424, filed on Sep. 26, 2000, and is a continuation-in-part-application of U.S. patent application Ser. No. 09/563,782 filed on May 2, 2000 and is also a continuation-in-part application of U.S. patent application Ser. No. 09/631,440, filed on Aug. 2, 2000.

BACKGROUND OF THE INVENTION

The invention relates to spectral analysis of biological analytes. More particularly the invention relates to an apparatus and method for minimizing spectral interference due to within and between sample variations during in-situ spectral sampling of tissue.

DESCRIPTION OF RELATED ART

Non-invasive, near IR diffuse reflectance measurement of glucose in human tissue requires sampling techniques that limit the degree of sampling error. The heterogenous and dynamic nature of living skin leads to sampling uncertainty in-vivo measurements. Sampling differences may arise due to variable chemical composition and light scattering properties in tissue. Because glucose is not uniformly distributed in tissue, a variation in the volume of tissue sampled is likely to lead to a variation in the strength of the glucose signal; the overall glucose concentration in tissue of blood remains constant. Variations in the placement and replacement of the fiber optic probe at the measuring surface can lead to changes in the optical sampling volume. A change in optical sampling leads to a variation in the glucose signal while blood glucose concentration remains unchanged.

Near infrared (NIR) tissue spectroscopy is utilized to irradiate the skin on the underside of a subject's extremity and estimate blood levels of biological analytes using a multivariate mathematical model. Mathematical analysis is used to extract significant spectral information about the net analyte signal. A large data set of samples from each subject is required to ensure a robust multivariate model. Spectral interferences within a measurement and between measurements lead to a decrease in the net analyte signal. As indicated above, sources of spectral interference include, but are not limited to, variation in location of the sample site and amount of pressure applied at the sample site. Furthermore, the physiological response of the tissue to contact with the measurement instrument is a significant source of sample variability. It is essential that known sources of spectral interference be minimized if a robust calibration model is to be developed.

P. Cooper and T. Barker, Individual calibration of blood glucose for supporting noninvasive self-monitoring blood glucose (sic), PCT application Ser. No. WO 98/37805 (Feb. 26, 1997) and J. Griffith, P. Cooper, T. Barker, Method and apparatus for non-invasive glucose sensing, U.S. Pat. No. 6,088,605 (Jul. 11, 2000) describe methods and apparati for non-invasive blood glucose determination. Spectroscopic samples are gathered at the subject's skin surface using a noninvasive glucose monitor. During sampling, the skin surface is repeatedly moved relative to the sampling probe, so that several samples are gathered, each from a slightly different measurement site. Provision is also made for raising and lowering the arm in a controlled manner relative to the sampling probe. While both references recognize that is desirable that the spectra making up calibration sets, test sets and subsequent sample spectra, be as free of noise from sampling factors as possible, they do not actually attempt to eliminate sampling error at the time of measurement by sampling in a reproducible manner. Rather, they attempt to ameliorate sampling error by averaging it out over several measurements. Furthermore, while they recognize that placement and pressure variations are important sources of spectral interference, they fail to address the problem of spectral interference caused by the physiological response of the subject's skin to contact with the measurement instrument. The described apparatus has no provision for adjusting the size and dimensions of the apparatus to individual subjects by providing replaceable components in a variety of shapes and sizes.

In a co-pending, commonly-assigned application, T. Blank, G. Acosta, M. Mattu, S. Monfré, Fiberoptic probe placement guide, U.S. patent application Ser. No. 09/563,782 (May 2, 2000) describe a placement guide for a fiber optic probe that comprises a mounting element shaped and dimensioned to approximate the contour of a subject's extremity, upon which a tissue measurement site is located. The mount includes a probe aperture into which the fiber optic probe is inserted to make contact with the tissue measurement site. While contact with the skin in the immediate vicinity of the measurement site is avoided, the mounting element rests atop the limb during use, possibly causing temperature transients near the tissue measurement site, due to physiological responses of the skin to contact with the placement guide and the probe. The guide is positioned by aligning cross hair slots around the aperture with crosshairs drawn on the subject's skin, rendering the probe guide better suited to short-term use in laboratory settings. The disclosed probe guide doesn't fully contemplate the importance of minimizing spectral effects related to pressure variations, since the fiber optic probe is inserted into the probe aperture as the mount rests atop the limb bearing the tissue measurement site, allowing for the possibility of pressure variations.

Another co-pending, commonly-assigned U.S. patent application, K. Hazen, G. Acosta, Apparatus and method for reproducibly modifying localized absorption and scattering coefficients at a tissue measurement site during optical sampling, U.S. patent application Ser. No. 09/631,440 (Aug. 2, 2000) describes an apparatus for modifying localized absorption and scattering coefficients by controlling the pressure applied to a tissue measurement site by an analyzer during optical sampling. The applied pressure may be maintained at a constant level, or it may be varied in a controlled, reproducible manner as a function of time, thus allowing absorption and reduced scattering coefficients to be varied in a controlled, reproducible manner. The device provides a placement guide for a limb bearing a measurement site that permits placement of the measurement site and pressure on the measurement site by the instrument to be reproducibly controlled. The described apparatus fails to contemplate, the importance, however of minimizing contact of the apparatus with the extremity bearing the measurement site to minimize the physiological response of the skin at the measurement site to contact with the apparatus. Furthermore, replaceable components in a variety of shapes and sized to adjust the apparatus to individual subjects are not provided.

It would be a great advantage to provide an apparatus and method for minimizing spectral interference during in-situ spectral sampling of tissue that enables the measurement site to be reproducibly positioned in relation to an optical coupling means, so that spectral interference related to placement and pressure variations is minimized. It would be a further advantage to provide such an apparatus in a minimal contact configuration, so that spectral interference related to contact of the measurement site with the apparatus is minimized. It would provide significant benefit if the apparatus were customizable to individual subjects; for example, by providing replaceable components custom-fabricated to a subject, or by providing replaceable components in a variety of shapes and sizes so that the apparatus may be adapted to subjects of different size or physiognomy.

SUMMARY OF THE INVENTION

The invention provides an apparatus and method for reproducibly interfacing a living tissue sample to the measurement probe of a spectrometer instrument in-situ, so that spectral interference related to sampling variations is minimized. A subject interface includes a base element having a plurality of supports mounted thereupon, each support providing a registration point on a subject's limb bearing a tissue measurement site. A probe aperture in the base element is provided through which an optical coupling means, such as a fiber optic probe, contacts the measurement site. In a preferred embodiment of the invention, elbow, wrist and hand supports are provided, spaced at ergonomically optimal intervals along the length of the base element. During use, the interface module is positioned on top of a spectrometer instrument with the measurement probe protruding upward toward the measurement site on the underside of the subject's arm. The supports have a minimal footprint so that contact with the skin of the arm is minimized. The interface module is adjustable, allowing it to be customized to any subject. In one embodiment, the supports are custom-fabricated to the subject. In another embodiment, the supports are provided in a variety of shapes and sizes. The various shapes and sizes may be combined to adjust the interface module to any subject. During use, the subject rests their arm on the support elements, so that the arm is reproducibly positioned and supported. Thus, spectral interference due to placement and pressure variations is minimized. The minimal contact of the support elements with the skin of the arm minimize spectral interference due to contact-induced temperature transients at the skin surface of the measurement site.

DETAILED DESCRIPTION

Figure 1:
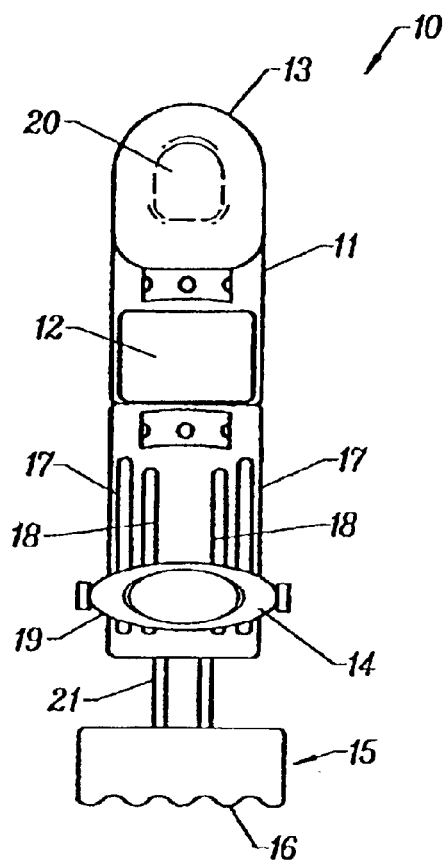
FIG. 1 provides a plan view of a subject interface module, according to the invention.

Spectroscopic estimation of blood analyte concentration is hampered by spectral interferences. Living human tissue is dynamic by nature and continuously undergoes changes in response to the environment. Physiological changes take place even while light is penetrating the tissue. Furthermore, shifts in the environment, such as temperature changes induce corresponding physiological changes in skin tissue. Interferences in spectral measurements at a tissue measurement site may be due to a variety of factors, among them skin temperature transients, variations in pressure applied to the skin at the measurement site, variations in tissue state, variations in positioning of the site relative to the spectrometer instrument, and others. Such sampling variations cause a reduction in the net analyte signal, which prevents the development of robust calibration models necessary for accurate estimates of biological analyte concentration. A novel subject interface module couples the subject's extremity bearing the tissue measurement site to the measurement probe of the spectrometer in such a way as to minimize spectral interferences within and between measurements. The subject interface module incorporates a minimal contact design to support and position the subject's extremity in a controlled and reproducible manner, thus addressing the following sources of spectral interference:

Within sample temperature transients. Living tissue undergoes a physiological temperature response upon coming into contact with environmental surfaces. Skin temperature may rise or fall, or a combination of both, depending on the temperature and heat capacity of the object the skin comes into contact with. Large skin temperature transients lead to increased spectral interference. The minimal contact subject interface module design provides support for the subject's extremity while minimizing the physiological response due to contact at the measurement site.

Pressure applied to the extremity at the measurement site. Pressure applied to living tissue impacts the localized thickness of the skin. Varying the force applied at the measurement site changes the tissue volume sampled by the beam of light emitted from the measurement probe. The subject interface module is designed to maintain consistent pressure in a reproducible fashion between the extremity and the measurement probe, thereby minimizing between sample variations in the tissue volume.

Positioning of the extremity in relation to the instrument. The subject interface module provides replaceable support elements to ensure that the subject's extremity is in a natural position and properly aligned with the measurement probe. The support elements may be custom fabricated for a subject or universal support elements in various shapes and sizes may be combined in various ways to adjust the subject interface module to any subject.

The support elements, along with the correct method of seating the extremity in the interface module, ensure that the extremity is reproducibly positioned and supported and that skin temperature transients due to contact of the extremity with the interface module are minimized.

In a preferred embodiment, the subject interface module is adapted to receive the arm of a human subject during noninvasive blood analyte determination using spectral analysis, such as Near IR. However, other embodiments consistent with the spirit and scope of the invention will be apparent to those skilled in the art of spectroscopic sampling techniques. For example, the principles of the invention may be employed to develop subject interface modules for veterinary use, or sample interface modules for use in spectroscopic analysis of fruits and vegetables. Furthermore, while the preferred embodiment is intended for use on live human subjects, it could also be used on the non-living, by pathologists for example.

FIG. 1 shows a plan view of the subject interface module 10 according to the preferred embodiment. A base element 11, having a top surface and a bottom surface is provided. During use, the subject interface module is placed on top of a spectrometer instrument (not shown). An aperture 12 in the base 11 provides a measurement probe (not shown) access to the underside of the subject's arm when the arm is seated in the interface module 10.

In this way, the subject interface module fits around a stationary measurement probe that is used to irradiate the skin. The co-pending U.S. patent application Ser. No. 09/631,440, supra, which is hereby incorporated by reference in its entirety, provides a detailed description of such a fiber optic probe. Light emitted from the probe travels through the heterogeneous layers of the tissue, where it is reflected and absorbed.

Elbow 13, wrist 14 and hand supports 15, are attached to the base element 11. As previously mentioned, the supports are replaceable. That is, they are easily removed and replaced with others. The supports may be custom-fabricated for a subject and attached to the base element when that subject is sampled. In another, equally preferred embodiment of the invention, universal supports are provided in a variety of shapes and sizes to accommodate a broad cross-section of individuals. The elbow support 13, attached at the proximal end of the base element 11, is molded such that it provides a cup-shaped depression 20 that closely mirrors the geometry of the elbow. In the case of custom-molded supports, the elbow support provides a near-exact negative impression of the subject's elbow. Universal elbow supports are provided in a variety of sizes to accommodate elbows of varying diameter. The universal elbow supports further include shims (not shown) of varying thickness, that may be placed between the base element and the elbow support, thereby allowing the height of the elbow support to be adjusted. It is desirable to adjust the height of the elbow support to accommodate arms of varying diameters, and so that downward pressure of the arm on the fiber optic probe may be varied in a controlled manner. Various methods of attaching the elbow support to the base may be used. Any method that allows the support to be securely attached and easily removed would be suitable; for example, a layer of pressure-sensitive adhesive applied to the support or to the base, VELCRO, various snap-in mechanisms or latching systems.

Figure 2:
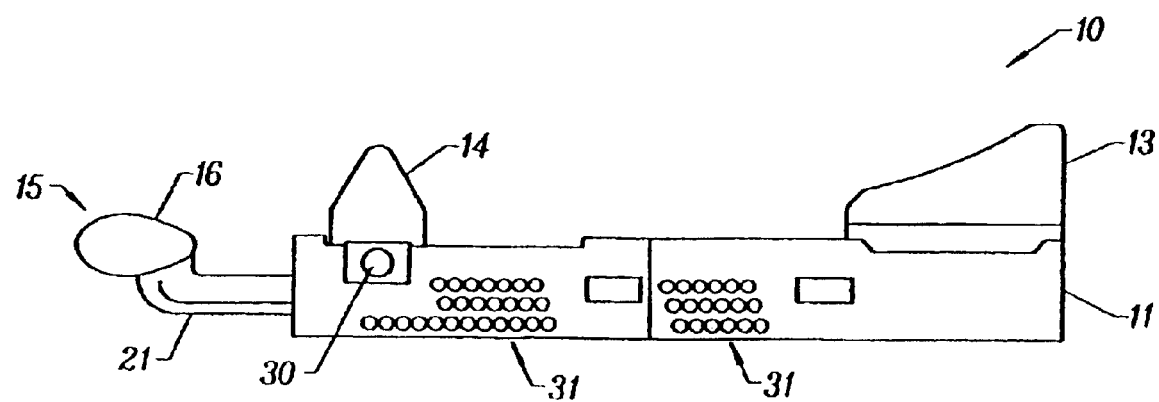
FIG. 2 provides a side elevation of the subject interface module of FIG. 1, according to the invention.

Toward the distal end of the base 11, a wrist support 14 provides a means of supporting the subject's wrist at the desired height while maintaining the arm in a natural position. A natural arm position is important for maintaining the subject's comfort, thereby minimizing the possibility that they will move the arm during sampling. The wrist support 14 is removably attached to a carrier element 30 (FIG. 2) mounted in parallel slots 17 in the base element 11 that permit the carrier element to be moved back and forth by sliding. In this way, the horizontal position of the wrist support can be adjusted. Various methods of attaching the wrist support to the carrier element are possible, for example, a bayonet type mechanism, a snapping mechanism or a threaded mechanism. During use, the wrist is rested on the wrist support such that it is received by an ergonomically shaped depression 19 that mirrors the contour of the wrist. As with the elbow support, the wrist rest may be custom fabricated for a particular subject, or universal supports may be provided in a variety of heights and contours to accommodate a broad cross-section of the subject population.

A hand support assembly 15 protrudes from the distal end of the base 11. In one embodiment of the invention, the hand support assembly is provided as a single structure. In an alternate embodiment of the invention, a hand support 16 is removably attached to a second carrier element 21. In either case, the hand support assembly 15 is mounted in a second pair of parallel slots 18, that allows the entire assembly to be retracted and extended in a slideable fashion, according to the length of the subject's arm. As with the other supports, the hand support is ergonomically contoured to mirror the shape of the hand and to support the hand such that a comfortable, natural hand position is encouraged. During use, the hand is rested on the hand support.

Indicators, such as graduated scales (not shown), or common measurement devices allow the horizontal position of the wrist and hand supports to be measured and recorded so that they may reproduced at any future time.

Patterns of circular openings 31 in the base provide an opportunity for free movement of air in the vicinity of the tissue measurement site. Additionally, the pairs of parallel slots 17 and 18 serve a second function of skeletonizing the base element as much as possible to facilitate air circulation. Thus, the possibility of skin temperature transients secondary to contact with the subject interface guide is further minimized.

In its current embodiment, the base element is fabricated from ABS (acrylonitrile butadiene styrene) plastic using conventional injection molding techniques, however other thermoplastic polymers would also be suitable. The supports may be fabricated from the same material, or they may be fabricated from an elastomeric substance that provides a resilient surface, such as RTV (room temperature vulcanizing) silicone putty. It is highly preferable that the invention be fabricated from thermally stable materials. That is, they tend to maintain a stable surface temperature.

Through the use of the supports, contact with the interface module by the subject's arm is restricted to the registration points where the supports contact the arm. In this way, thermal transients at the skin surface due to contact with the measuring instrument are greatly minimized.

In the case of custom-fabricated supports, reproducibly supporting and positioning the arm for future samples is readily achieved by attaching the subject's supports and restoring the wrist and hand supports to the previously recorded position for that subject. In the case of universal supports, the sizes and shapes of the parts used to achieve the desired placement for that subject are recorded, and those same parts are used for future samples.

Once the subject's arm is properly positioned, sampling occurs by directing light emitted from a radiation source toward the tissue measurement site through a fiber optic probe. The light that is reflected back is collected and represents a data point that contains spectral information about the tissue volume it has traveled through. Multiple data points comprise a data set, which is required for calibration development. By using the subject interface module to position the subject's arm, spectral interferences from the sampling variations already described are greatly minimized, thus facilitating the process of obtaining reproducible data points. Minimizing interferences optimizes the signal-to-noise ratio, allowing the development of robust calibration models, which in turn produces more accurate estimations of analyte concentration.

EXPERIMENT

An experiment was performed to analyze skin temperature variation due to arm contact with a subject interface module. Several subject interface module contact configurations were investigated to improve the subject interface module design from a thermal stability perspective. The results of this investigation show that minimal contact between the subject interface module and arm is desirable.

Introduction

Previous investigations have shown that the amount of contact between the subject interface module and an arm has a significant influence on the skin temperature transients that occur during the course of a noninvasive measurement. A full contact subject interface module was modified so that the only contact points between the arm and the subject interface module are at the elbow, wrist, hand, and the spectral measurement site. In addition, this modified subject interface module provides for custom supports at the contact points through the use of a mold that can be made for each subject.

Experimental

Prior to the modifications made to the subject interface module, skin temperature response to subject interface module contact was collected using seven subjects with a full-contact subject interface module. The same subjects were also tested on a third subject interface module, also providing minimal contact at the elbow, wrist, and hand.

Noninvasive spectra were collected for seven subjects using a fiber optic coupled spectrometer instrument with the modified subject interface module.

A YSI (YELLOW SPRINGS INSTRUMENTS of Yellow Springs Ohio.) pediatric temperature probe was used to measure each subject's skin temperature close to the spectral measurement site. Ambient skin temperature was monitored prior to data collection to ensure a stable starting temperature. Four replicates were collected for each subject using lab software with a total of 16 spectra pairs per replicate. Temperatures were recorded for each forward raster scan during collection. The total scan time per replicate was approximately 2 minutes.

Results

Initial results from this study indicate a reduction in skin temperature transients with the modified subject interface modules. Table I presents the maximum temperature change for subjects tested along the subject's forearm over 90 second intervals on three different subject interface modules: the full-contact subject interface module, the first modified subject interface module (minimal contact), and the second modified subject interface module (minimal contact).

TABLE 1

Maximum temperature differences ($T_{max} - T_{min}$) over 90 seconds of contact

| | Full-contact | Modified (to produce minimal contact) full contact | Minimal contact |
|---|---|---|---|
| | 0.50 | 0.16 | 0.05 |
| | 0.50 | 0.21 | 0.20 |
| | 0.80 | 0.19 | 0.05 |
| | 0.90 | 0.19 | 0.10 |
| | 1.10 | 0.41 | 0.20 |
| | 0.75 | 0.16 | 0.30 |
| | 0.35 | 0.20 | 0.10 |
| Average | 0.70° F. | 0.217° F. | 0.143° F. |

Large temperature transients have been observed during approximately the first 30 seconds of subject interface module contact and, therefore, have been excluded from this analysis. It should be noted that due to the requirement of custom molds for the modified full-contact subject interface module, the subjects tested on the modified subject interface module were not all the same as those tested on the full contact and minimal contact subject interface modules. Assuming the two populations are equal, an F-test at 99% confidence shows that there is a difference between the temperature range of the Full Contact subject interface module and the modified subject interface module. In addition, at 99% confidence, there is no difference between the modified full contact subject interface module and the minimal contact subject interface module.

Discussion

The analysis shows that arm contact on the modified full contact subject interface module leads to a smaller range of skin temperature transients than does the full contact subject interface module. The modified full contact subject interface module ranges are slightly higher than those of the minimal contact subject interface module. This could possibly be due to the differences in the amount of contact at the elbow support. The customized elbow supports used on the modified full contact subject interface module provide for more contact than the generic elbow support of the minimal contact subject interface module.

Although the invention has been described herein with reference to certain preferred embodiments, one skilled in the art will readily appreciate that other applications may be substituted without departing from the spirit and scope of the present invention. Accordingly, the invention should only be limited by the claims included below.

What is claimed is:

1. An interlace module for limiting sampling variation during in-situ spectral sampling at a tissue measurement site on an arm of a live subject, comprising:

a base having a top surface, a bottom surface and opposing ends, said base defining an aperture that communicates from said bottom surface to said top surface;

an elbow support, said elbow support replaceably attached to said top surface at a first of said opposing ends;

a wrist support said wrist support replaceably attached to said top surface toward a second of said opposing ends; and a hand support, said hand support slideably attached to said base at said second of said opposing ends and protruding from said opposing end;

said interface module configured to receive said arm so that said arm is supported in a comfortable position and reproducibly positioned in relation to a fiber optic probe;

wherein said supports limit contact of said arm with said interface module to distinct registration points; and wherein said interface module is customizable to individual subjects.

2. The interface module of claim 1, wherein said sampling variation comprises either of:

within sample interference; and interference between samples.

3. The interface module of claim 1, wherein said sampling variation results from any of:

variation in placement of said arm in relation to said optical coupling means between samples;

variation in pressure applied by said optical coupling means to said tissue measurement site within or between samples; and surface temperature transients, at said tissue measurement site, caused by contact of said arm with said interface module within a sample.

4. The interface module of claim 1, wherein said interface module is positioned during use such that said probe is received by said aperture at said bottom surface and protrudes through said top surface to make contact with said tissue measurement site when said arm is seated in said interface module.

5. The interface module of claim 1, wherein said elbow support includes a depression that approximately mirrors the shape of an elbow, wherein said elbow is received by said depression when said arm is seated in said interface module, so that said elbow is reproducibly positioned and supported, said elbow support being provided in a plurality of shapes and sizes, according to diameter of said elbow.

6. The interface module of claim 1, wherein said elbow support further comprises one or more shims for adjusting elbow height, said shim being placed beneath said elbow support, and wherein said shim is provided in a plurality of thicknesses.

7. The interface module of claim 1, wherein said wrist support provides a surface upon which a wrist is rested during use, so that said wrist is reproducibly positioned and supported, and wherein said wrist support is provided in a plurality of heights and contours.

8. The interface module of claim 1, wherein said hand support provides a surface upon which a hand is rested during use, so that said hand is reproducibly positioned and supported; and wherein said hand support is slideably adjustable so that a variety of arm lengths may be accommodated.

9. The interlace module of claim 1, wherein said supports are custom-fabricated for a specific subject.

10. The interface module of claim 1, said interface being fabricated from one or both of:

one or more thermoplastic polymers; and one or more elastomeric polymers.

11. An interface module for limiting sampling variation during in-situ spectral sampling at a tissue measurement site, comprising:

a base having two opposing surfaces and two opposing ends;

a plurality of support elements mounted on said base, wherein said support elements are adapted to receive a member bearing said tissue measurement site so that said tissue measurement site is reproducibly positioned and supported in relation to an optical coupling means, wherein said supports limit contact of said member with said interface module to distinct registration points; and wherein said interface module is adjustable to individual subjects.

12. The interface module of claim 11, wherein said sampling variation comprises either of:

within sample interference; and interference between samples.

13. The interface module of claim 11, wherein said sampling variation results from any of:

variation in placement of said member in relation to said optical coupling means between samples;

variation in pressure applied by said optical coupling means to said tissue measurement site within or between samples; and surface temperature transients at said tissue measurement site, caused by contact of said member with said interface module within a sample.

14. The interface module of claim 11, wherein said base defines an aperture communicating from a first of said surfaces to a second of said surfaces.

15. The interface module of claim 14, said optical coupling means comprising a fiber optic probe, wherein said interface module is positioned during use such that said probe is received by said aperture at said first surf and protrudes through said surface to make contact with said tissue measurement site when said member is seated in said interface module.

16. The interface module of claim 15, wherein said member comprises an arm on a human subject.

17. The interface module of claim 16, wherein said support elements include one or more of:

an elbow support;

a wrist support; and a hand support.

18. The interface module of claim 17, wherein said elbow support is replaceably attached to said top surface at a first of said opposing ends.

19. The interface module of claim 17, wherein said elbow support includes a depression that approximately mirrors the shape of an elbow, wherein said elbow is received by said depression when said arm is seated in said interface module, so that said elbow is reproducibly positioned and supported.

20. The interface module of claim 19, wherein said elbow support further comprises means for adjusting elbow height.

21. The interface module of claim 20, wherein said means for adjusting elbow height comprises at least one shim, wherein said shim is placed beneath said elbow support, and wherein said shim is provided in a plurality of thicknesses.

22. The interface module of claim 17, wherein said elbow support is provided in a plurality of shapes and sizes, according to diameter of said elbow.

23. The interface module of claim 17, wherein said wrist support is replaceably attached at said top surface of said base toward a second of said two opposing ends.

24. The interface module of claim 17, wherein said wrist support provides a surface upon which a wrist as rested during use, so that said wrist is reproducibly positioned and supported.

25. The interface module of claim 17, wherein said wrist support is provided in a plurality of heights and contours.

26. The interface module of claim 17, wherein said hand support is slideably attached to said base at said second of said opposing ends and protruding from said second end, wherein said hand support is slideably adjustable so that a variety of arm lengths may be accommodated.

27. The interface module of claim 17, wherein said hand support provides a surface upon which a hand is rested during use, so that said hand is reproducibly positioned and supported.

28. The interface module of claim 17, wherein said supports are custom-fabricated to a specific subject.

29. The interface module of claim 11, said interface being fabricated from one or both of:

one or more thermoplastic polymers; and one or more elastomeric polymers.

30. A method of limiting sampling variation during in-situ spectral sampling at a tissue measurement site comprising the steps of:

minimizing variation in placement of a tissue measurement site in relation to an optical coupling means by means of one or more support elements that receive a member bearing said tissue measurement site, so that substantially the same region is sampled at each measurement;

minimizing variation in pressure applied by art optical coupling means to said tissue measurement site so that substantially the same volume of tissue is displaced at each measurement; and minimizing surface temperature transients at said tissue measurement site by minimizing contact of said member with said interface module so that temperature remains substantially constant for each measurement;

wherein signal-to-noise ratio is optimized to facilitate signal detection.

31. The method of claim 30, wherein said step of minimizing variations in placement of said issue measurement site comprises reproducibly positioning a member bearing said tissue measurement site in relation to said optical coupling means.

32. The method of claim 31, wherein said step of minimizing variations in pressure applied by said optical coupling means to said tissue measurement site comprises reproducibly supporting said member in relation to said optical coupling means.

33. The method of claim 32, further comprising the step of providing a minimal contact subject interface module, said subject interface module comprising:

a base having two opposing surfaces and two opposing ends;

a plurality of support elements mounted on said base, wherein said support elements are adapted to receive said member beating said tissue measurement site so that said issue measurement site is reproducibly positioned and supported in relation to said optical coupling means; and wherein said supports minimize contact of said tissue measurement site with said interface module.

34. The method of claim 33, wherein said base defines an aperture communicating from a first of said surfaces to a second of said surface.

35. The method of claim 34, said optical coupling means comprising a fiber optic probe wherein said interface module is positioned during use such that said probe is received by said aperture at said first surface and protrudes through said second surface to make contact with said tissue measurement site when said member is seated in said interface module.

36. The method of claim 35, wherein said member comprises an arm on a human subject.

37. The method of claim 36, wherein said support elements include one or more of:

an elbow support;

a wrist support; and a hand support.

38. The method of claim 37, wherein said elbow support is replaceably attached to said top surface at a first of said opposing ends.

39. The method of claim 37, wherein said elbow support includes a depression that approximately mirrors the shape of an elbow, wherein said elbow is received by said depression when said arm is seated in said interface module, so that said elbow is reproducibly positioned and supported.

40. The method of claim 37, wherein said elbow support is provided in a plurality of shapes and sizes, according to diameter of said elbow.

41. The method of claim 40, wherein said elbow support further comprises means for adjusting elbow height.

42. The method of claim 41, wherein said means for adjusting elbow height comprises at least one shim, wherein said shim is placed beneath said elbow support, and wherein said shim is provided in a plurality of thicknesses.

43. The method of claim 37, wherein said wrist support provides a surface upon which a wrist is rested during use, so that said wrist is reproducibly positioned and supported.

44. The method of claim 37, wherein said wrist support as provided in a plurality of heights and contours.

45. The method of claim 37, wherein said hand support is slideably attached to said base at said second of said opposing ends and protruding from said second end, wherein said hand support is slideably adjustable so that a variety of arm lengths may be accommodated.

46. The method of claim 37, wherein said hand support provides a surface upon which a hand is rested during use, so that said hand is reproducibly positioned and supported.

47. The method of claim 37, wherein said supports am custom-fabricated for a specific subject.

48. An interface module for limiting sampling variation during in-situ spectral sampling at a tissue measurement site, comprising:

one or more support elements, wherein said one or more support elements are adapted to receive a member bearing said tissue measurement site so that said tissue measurement site is reproducibly positioned and supported in relation to an optical coupling means, wherein said one or more support elements limit contract of said member with said interface module to distinct registration points.

49. The interface module of claim 48, further comprising a base, wherein said one or more support elements are mounted on said base.

50. A method of limiting sampling variation during in-situ spectral sampling at a tissue measurement site comprising the steps of:

minimizing variation in placement of a tissue measurement site in relation to an optical coupling means, so that substantially the same region is sampled at each measurement; and minimizing variation in pressure applied by an optical coupling means to said tissue measurement site by liming contact of a member bearing said tissue measurement site to distinct registration points, so that substantially the same volume of tissue is displaced.

51. The method of claim 50, further comprising a step of:

minimizing surface temperature transients at said tissue measurement site so that temperature remains substantially constant for each measurement.

52. The method of claim 50, wherein signal-to-noise ratio is optimized to facilitate net analyte signal detection.

53. A method of limiting sampling variation during in-situ spectral sampling at a tissue measurement the comprising the steps of:

minimizing variation in placement of a tissue measurement site in relation to as optical coupling means by means of one or more support elements that receive a member bearing said tissue measurement site, so that substantially the same region is sampled at each measurement; and minimizing surface temperature transients at said tissue measurement site, by limiting contact of a member bearing said tissue measurement site with a subject interface module, so that temperature remains substantially constant for each measurement.

54. The method of claim 53, further comprising a step of:

minimizing variation in pressure applied by an optical coupling means to said tissue measurement site so that substantially the same volume of tissue is displaced.

55. The method of claim 53, wherein signal-to-noise ratio is optimized to facilitate net analyte signal detection.

* * * * *